US005141433A

United States Patent [19]

Peterson

[11] Patent Number: 5,141,433

[45] Date of Patent: Aug. 25, 1992

[54] DENTAL ARTICULATOR

[76] Inventor: Kenneth N. Peterson, 14210 Rim Rock Rd., Reno, Nev. 89511

[21] Appl. No.: 520,070

[22] Filed: May 7, 1990

[51] Int. Cl.[5] .............................................. A61C 11/00

[52] U.S. Cl. .......................................... 433/64; 433/57

[58] Field of Search ..................................... 433/57, 64

[56] References Cited

U.S. PATENT DOCUMENTS

| | | | |
|---|---|---|---|
| 537,812 | 4/1895 | Bragg | 433/64 |
| 981,430 | 1/1911 | Kennedy | 433/64 |
| 1,736,006 | 11/1929 | Hagman | 433/64 |
| 3,078,577 | 2/1963 | Prentki | 433/64 |
| 3,414,977 | 12/1968 | Cayo | 433/57 |
| 4,352,662 | 10/1982 | Lee | 433/57 |
| 4,449,930 | 5/1984 | Huffman | 433/64 |
| 4,511,332 | 4/1985 | Mack | 433/59 |
| 4,537,574 | 8/1985 | Clark | 433/69 |
| 4,573,915 | 3/1986 | Merz | 433/64 |
| 4,601,664 | 7/1986 | Bertino | 434/264 |
| 4,687,442 | 8/1987 | Wong | 433/63 |
| 4,758,155 | 7/1988 | Marino | 433/58 |
| 4,764,113 | 8/1988 | Hiranuma | 433/56 |
| 4,781,586 | 11/1988 | Lisec | 433/57 |
| 4,797,097 | 1/1989 | Cohn | 433/64 |
| 4,854,868 | 8/1989 | Pitre | 433/60 |

*Primary Examiner*—John J. Wilson
*Attorney, Agent, or Firm*—Brian C. Kelly

[57] ABSTRACT

A dental articulator with its condyle joint being a single ball attached to the upper support member and being removable as well as rotatable through 360 degrees, with the ball being supported in a spring loaded cylinder, allowing the technician to position the upper support member in multiple positions without the need of locking screws. Also, the incisal guide pin is located behind the models to give an unobstructed work area and a unique retaining method is provided which leaves an imprint on the plaster mold so that the molds can only be replaced in one position.

32 Claims, 5 Drawing Sheets

24 68 26 18 66 38 28 40 56 14 36 32 58 42 12 44 52 60 56 48 62 58 56 46 56 52 58 64 58 54 56 64 58 10 56

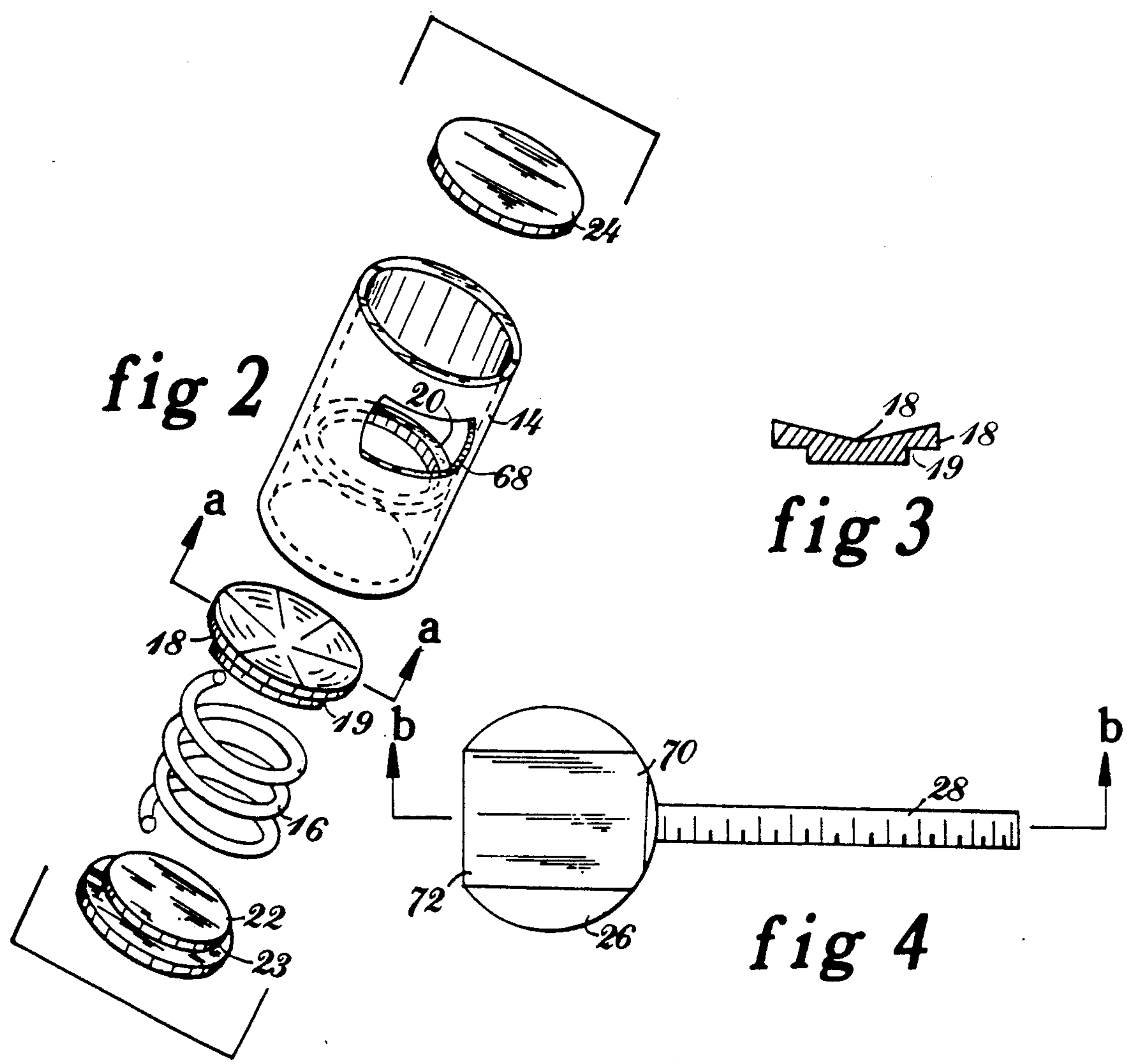
fig 2
24
20
14
68
a
a
18
19
16
22
23
18
18
19
fig 3
b
b
70
28
72
26
fig 4
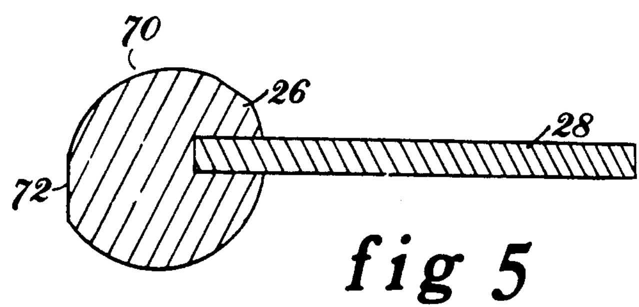
70
26
28
72
fig 5

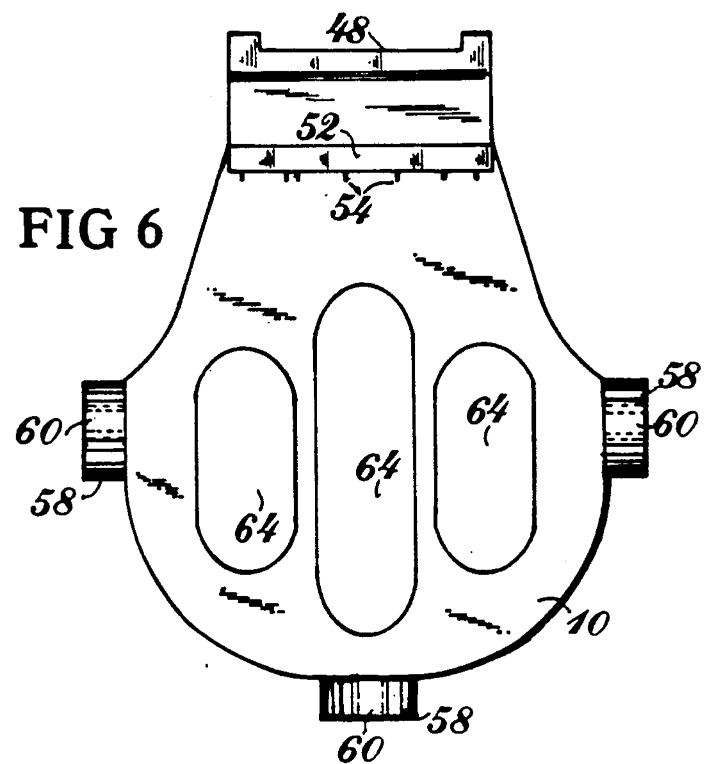
FIG 6
FIG 7
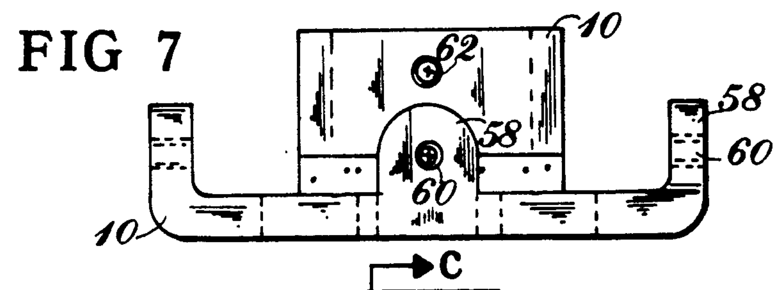
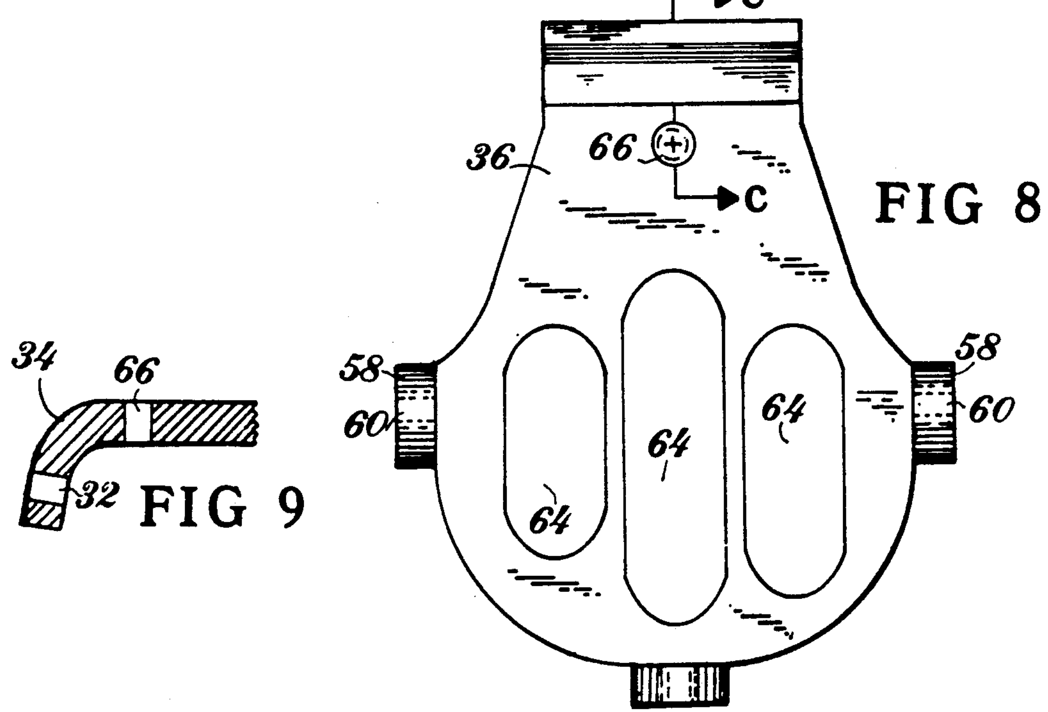
FIG 8
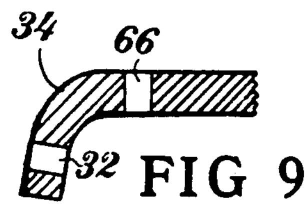
FIG 9

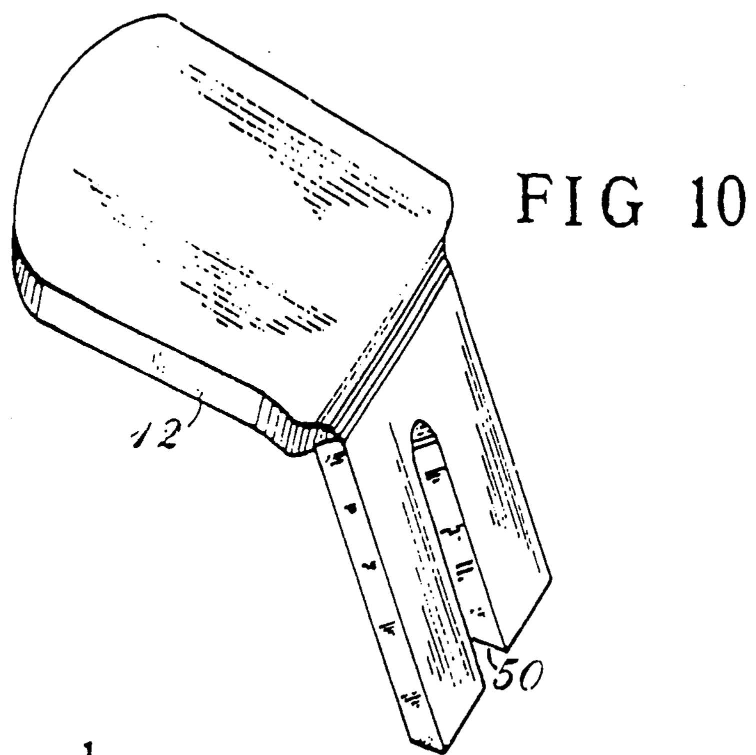
FIG 10
12
50
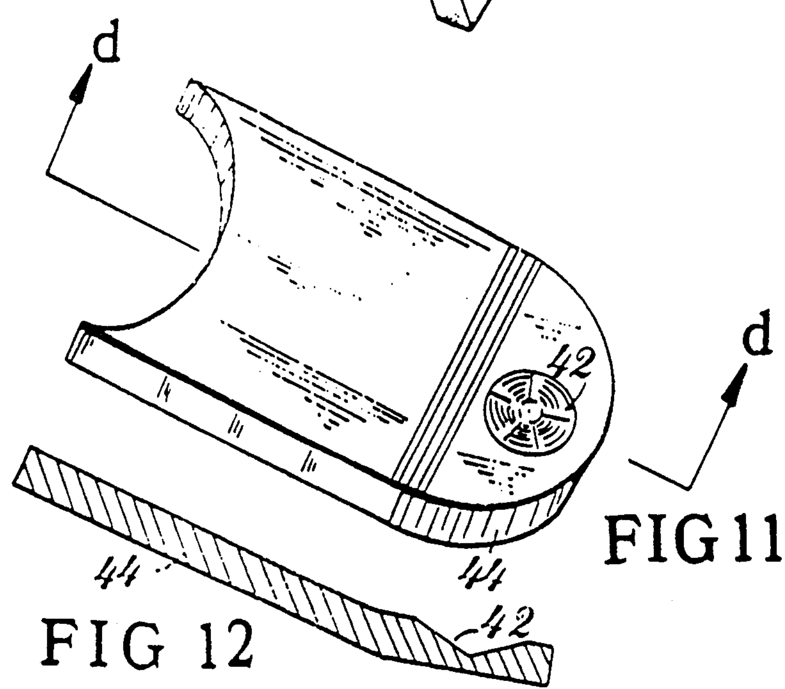
d
d
42
FIG 11
44
44
42
FIG 12

DENTAL ARTICULATOR

FIELD OF THE INVENTION

This invention relates to dental articulators and specifically to articulators for use in modeling or simulating the movement of the human jaw.

BACKGROUND OF THE INVENTION

Dental articulators have been taught for many years and are in wide spread use all over the world and designs range from a simple throw-away version to highly complicated mechanisms encluding electronically controlled jacks and other costly devices costing thousand of dollars.

Several types of articulators are known. One common type is the axle and track articulator manufactured by Hanau Engineering Company. An axle and track has an upper frame and a lower frame, with slots or tracks on the lower frame carrying an axle removably attached to the upper frame.

A second type of articulator is the articulator-condyle or "arcon" type. Arcon artiulators are characterized by a lower frame carrying a pair of condyle balls and an upper frame having guides which receive the condyles and permit the upper frame to pivot and slide on the condyle and move to closely simulate human jaw movements.

One important characteristic of a dental articlulator is the ability to closely simulate the actual centrix, lateral and protrusive jaw movements of the patient in order that the prosthodonist may produce a comfortable and effective dental prosthesis.

Even though the prior art is quite extensive, many problems still exist in the art which the present invention addresses.

One problem which exists in many models is accessibility which is addressed in different manners such as U.S. Pat. No. 4,290,754 which provides for a single, slender arm or support post for the condylar mechanisms which helps in reaching the back section of the teeth models however the incisor guide pin is still in front of the anterior teeth causing an obstruction. U.S. Pat. No. 4,854,868 addresses this problem by providing the incisor guide pin in the form of a horizontal U but still leaves the anterior teeth in an awkward position to be reached by the technician.

Another problem is mounting the models in the articulator so that they can be removed in the same relationship and a number of complicated means are taught such as U.S. Pat. No. 4,169,314 that requires a threaded aperture embedded into the base of the cast. U.S. Pat. No. 4,744,751 teaches a mechanical apparatus which requires two removable fixtures attached to the articulator with additional orientation means.

Yet another problem encountered in most articulators is the lack of the ability to completely remove the top model from the lower model without disassembling the device.

Still another inherent problem especially in the arcon style of articulators is the drawback of the large distance between the two hinge joints locked at the lateral axis. U.S. Pat. No. 4,536,161 attempts to solve this problem by a complicated spring, cam and cam follower arrangement between the pivot arm and the base.

SUMMARY OF THE INVENTION

It is a primary object of the present invention to provide an articulator which closely and accurately simulates the actual centric, lateral and protrusive jaw movements of the patient in order that the prosthodontist may produce a comfortable and effective dental prosthesis.

It is another object to provide accessibility to the anterior teeth without having to work around any obstruction such as the incisor guide.

Yet another object is to provide an articulator that uses only one condyle mechanism that allows freedom of movement in all directions.

Still another object is to provide an articulator in which the top plate with its model can be easily removed from its condyle mechanism and yet when replaced will again be in its centric position.

Another object is to provide a condyle mechanism that is a single ball which is removably retained in a spring loaded cylinder with the lower extremes of the ball being seated in a concaved, spring loaded portion and its top section being substantially flattened riding on an upper surface corresponding with the rise of the incisor guide pin.

Still another object is to so construct the condyle mechanism in such a manner that the top model will stay in most fixed positions as set by the technician without the need of locking screws or the like.

Yet another object is to provide a secondary position of the articulator which allows the device to lay back and support itself so that the upper and lower models are substantially at a 45 degree angle and the technician can face the teeth "straight on".

Another object is to provide a design which allows the top plate with its model attached to rotate 360 degrees.

Still another object is to provide access slots in the top and bottom plates for easy access to dowel pins.

Yet another object is to provide adjusting and retaining screws on the top and bottom models in a fixed relationship.

Also another object is to provide means to adjust the height or the distance between the top and bottom plates.

Still another object is to provide an articulator which has a non-glare surface such as sand blasted plastic and of a configuration that makes it conducive to injection molding, casting or fabrication.

Another important object is to provide an articulator that due to its adjustability can be used for plaster or plasterless models.

Yet another object is to provide an articulator that can be depressed at the spring loaded condyle mechanism to check for proper occlusion or bite.

Other objects and advantages will become apparent when taken into consideration with the following drawings and specifications.

BRIEF DESCRIPTION OF THE DRAWINGS

FIG. 2 is an exploded view of the cylinder and its components.

FIG. 3 is a section taken at a—a of FIG. 2.

FIG. 4 is a top view of the condyle ball joint and its mounting means.

FIG. 5 is a section taken at b—b of FIG. 4.

FIG. 6 is a top view of the bottom member.

FIG. 7 is an end view of the bottom member.

FIG. 8 is a top view of the top member.

FIG. 9 is a section taken at c—c of FIG. 8.

FIG. 10 is a perspective view of the adjustable cylinder mounting member.

FIG. 11 is a perspective view of the support member and indent for the incisor guide pin.

FIG. 12 is an section taken at c—c of FIG. 11.

DETAILED DESCRIPTION OF THE DRAWINGS

Figure 1:
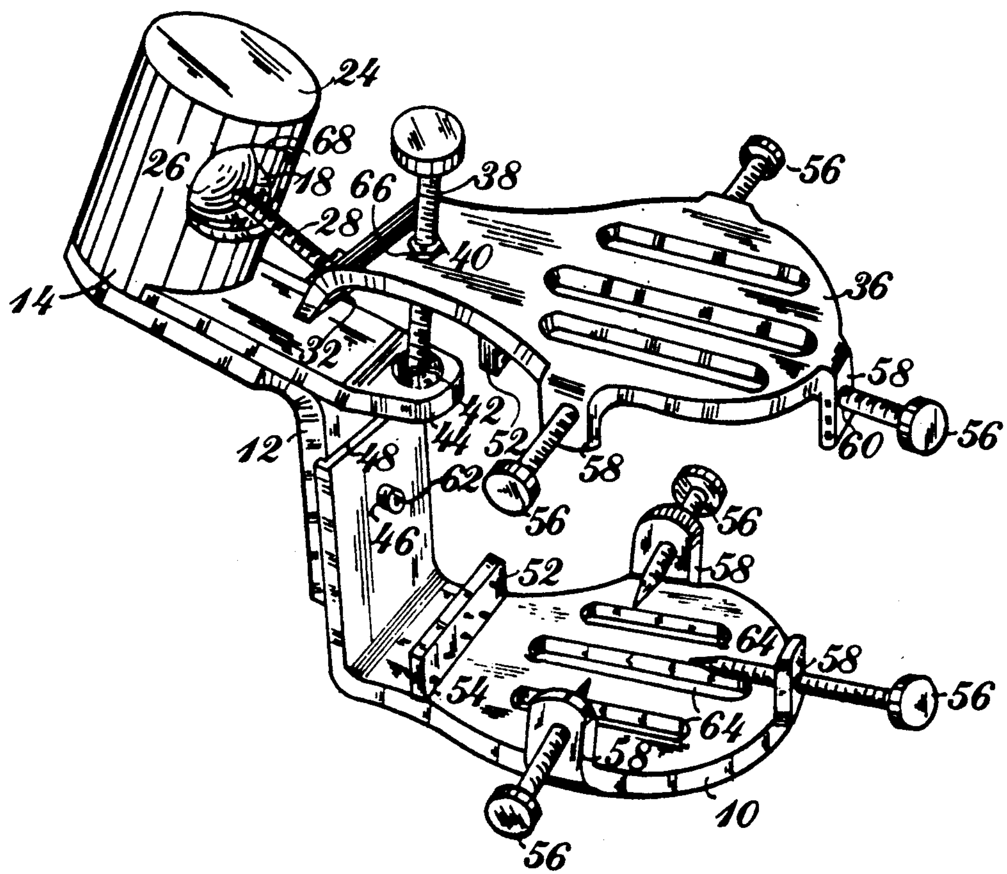
FIG. 1 is a perspective view of the present invention.
Figure 13:
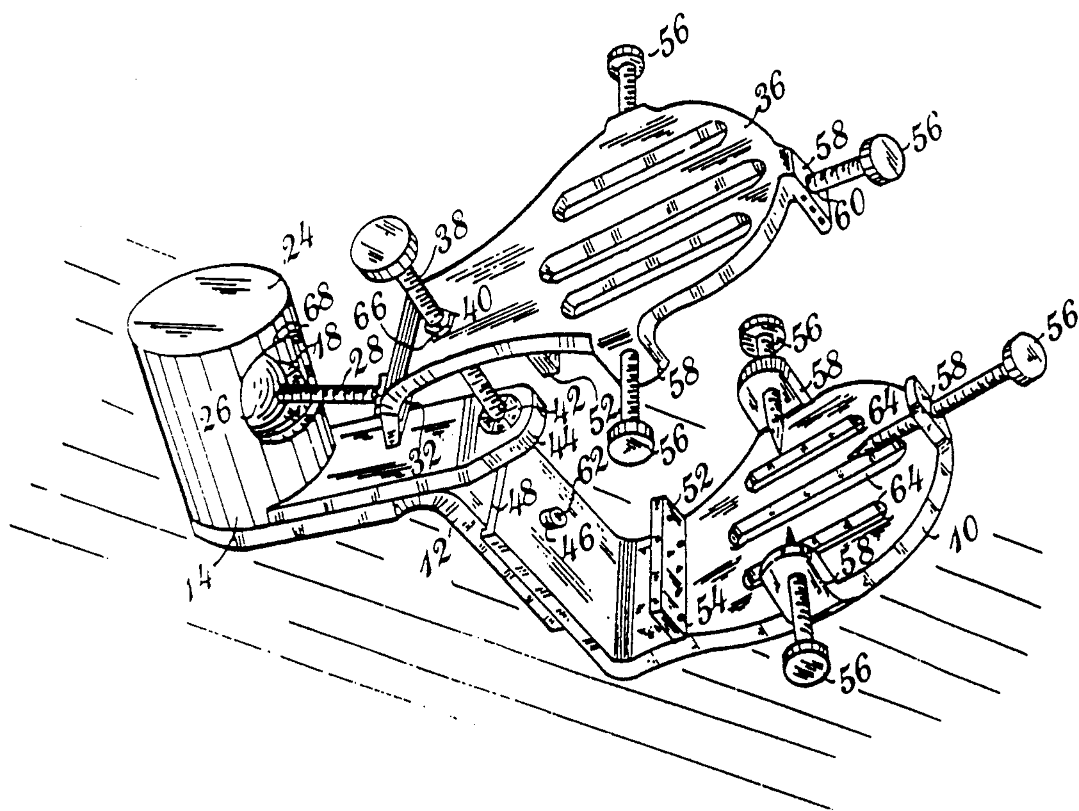
FIG. 13 is a perspective view showing the present invention setting on a surface at an angle and in a leaned back position, supported by the bottom support member and the bottom of the cylinder support member.

Referring now to the drawings in detail wherein like numerals represent like parts, 10 is a lower support member which supports adjustable support member 12, while 14 is a substantially hollow cylinder suitable affixed to member 12 and 44 which houses spring 16 and ball seat 18, with ball seat 18 being held by spring 16 against internal ring 20, ring 20 being a part of or suitably affixed to cylinder 14. The spring is held in a tensioned state between internal ring 20 and end plate 22, the end plate 22 being suitably affixed to cylinder 14, while 24 is a top cylinder end plate suitably affixed to cylinder 14.

26 is substantially a ball with 28 being a threaded shaft and jam nut 30 removably and adjustably affixing shaft 28 into threaded mounting hole 32 located in the curved portion 34 of upper support member 36, while 38 is an incisor guide pin mounted in threaded hole 66 with its adjustable jam nut 40 and guide pin 38 resting on indentation 42, which is formed in support member 44, support 44 being suitably affixed to adjustable support member 12, support member 12 being held in a secure manner by adjusting screw 46 in recessed slot 48 and elongated slot 50 of support member 12.

The plastic molds are also held secure by retaining thumb screws 56 which are mounted on suitable mounting supports 58 through threaded holes 60. 64 are open adjusting slots through which the technician may work to insert dowel pins and the like, into the workpieces, while 65 is an open slot in cylinder 14 to allow the ball 26 to move freely and also allow the ball assembly and upper support member to be inserted or removed at will. 70 is a substantially flat section on ball 26 which allows the ball 26 to work and seat against the top end plate 24 while 72 is a flat section on the ball which allows the ball to be moved deeper into the back section of cylinder 14, while 19 and 23, respectively, are seats for spring 16 in ball seat and spring stop 18 and end plate 22, respectively.

The point of the thumbscrews also are embedded into the plaster molds and can be seated in only one position.

It will also be seen that the technician can now move the upper support member and its associated mold in centrix, lateral and protrusive movements that more accurately simulate the true movements of the human jaw.

It will also be noted that the technician has full access to the models as there are no obstructions either on the sides or in the front of the anterior teeth as the incisor guide pin has been located in the back of the models.

It will also be observed that we have provided an articulator that uses only one condyle mechanism that allows freedom of movement in all directions.

Also the technician can now remove the entire upper support member with its associated model firmly attached and work on the work piece which is now entirely removed from the lower support member which, with its associated model, is now entirely exposed also and yet, when the ball of the upper support member is again placed into the cylinder, the upper support member with its associated model returns to its original, centrix position.

It will also be seen that the condyle mechanism now holds a single ball in a moveable, yet firm position and allows the technician to move the model to any position desirable to comfortably work on the workpieces, with no need of locking screws.

Also, the technician at will can tilt the articulator to a second, laid back position so that he can face and work on the models "straight on".

Another important advantage achieved is that the technician can rotate the upper support member and its model a full 360 degrees at will.

We have also provided access slots in the upper and lower support members to allow the technician to easily have access to dowel pins at will.

Also, another important advantage which the present invention achieves is the adjustability of the height of the upper support member in relation to the lower support member, thus allowing the technician to use relatively thin or thick plaster molds.

We have also taught that the articulator may be made with a non-glare surface such as sand blasted plastic, and be made of a configuration that makes it hand friendly and easy to hold.

We have also provided a design that may be fabricated or is conducive to injection molding or casting.

Another very important advantage that the present invention achieves is that proper occlusion or bite may now be checked by simply depressing the spring loaded condyle mechanism.

Although the invention has been shown and described in what is conceived to be the most practical and preferred embodiment, it is recognized that departures may be made therefrom within the scope and spirit of the invention which is not to be limited to the details disclosed herein but it is to be accorded the full scope of the claims so as to embrace any and all equivalent devices and apparatus.

Having described our invention, what we claim as new and desire to secure by Letters Patent is:

1. A dental articulator comprising; a second support member and a first support member, said second member comprising at its posterior a vertical rising member, said vertical rising member comprising means releasably supporting an angular member, said angular member at its posterior supporting a cylinder, said cylinder housing a spring, said spring having a lower and a upper retaining means to hold said spring in a state of tension, said upper retaining means having stop means in said cylinder, said upper retaining means being movable in said cylinder, said upper retaining means on its distal side having a ball seat, a ball, said ball seat cooperating with said ball to form a condylar joint, said ball being captured between said ball seat and an upper cylinder end member, said end member cooperating with said cylinder to close said cylinder, said cylinder having an opening on its anterior side, said opening being of sufficient size to allow the ingress and egress of said ball, said ball having means affixed to a shaft, said shaft having means at its distal end affixed to said first support member, said first support member having at its posterior means supporting an incisal guide pin, said guide pin resting on an extension of said angular member, said extension having an indentation cooperating with the lower end of said guide pin, said guide pin controlling the distance between said second member and said first member, and said second member and said first member having retaining means to releasably hold denture models.

2. The device of claim 1 in which said second and first support members have at least one aperture.

3. The device of claim 2 in which said aperture is a slot.

4. The device of claim 1 in which said means releasably supporting said angular member to said vertical rising member comprises a dovetail joint between said vertical rising member and said angular member, said dovetail joint being secured by a fastener.

5. The device of claim 4 in which said dovetail join comprises length adjustment means disposed between said lower support and said angular member.

6. The device of claim 5 in which said length adjustment means comprises at least one slot in one of said members.

7. The device of claim 1 in which said ball seat comprises a conical V shape.

8. The device of claim 1 in which said ball comprises a substantially flat rounded portion, said portion cooperating with said upper cylinder end member to form a horizontal working joint.

9. The device of claim 1 in which said ball comprises on its side opposite said shaft a substantially flat portion, said flat portion allowing said ball to be inserted closer to the back wall of said cylinder than if said ball was conical.

10. The device of claim 1 in which said opening in said cylinder comprises an elongated opening.

11. The device of claim 1 in which said means to affix said ball to said shaft comprises threads.

12. The device of claim 1 in which said means to affix said shaft to said first support member comprises threads and a jam nut.

13. The device of claim 1 in which said means to support said incisal guide pin comprises threads.

14. The device of claim 1 in which said incisal guide pin comprises adjustable means.

15. The device of claim 1 in which said adjustable means comprises threads and a jam nut.

16. The device of claim 1 in which said indentation on said extension of said angular member comprises a conical V shape.

17. The device of claim 1 in which one planar surface of said conical V shape of said indentation substantially corresponds to the planar surface of said upper end member of said cylinder.

18. The device of claim 1 in which said retaining means in said lower and upper support members include at least one thumb screw.

19. The device of claim 18 in which said retaining means comprises a point capable of penetrating and holding said denture models.

20. The device of claim 18 in which said thumb screw is made of metal.

21. The device of claim 1 in which said first member is removable.

22. The device of claim 1 in which said first member is rotatable through 360 degrees.

23. The device of claim 1 in which said dental articulator has a first and second position, said first position being with the said second support member laying horizontally on a surface, said second position being with said articulator being in a laid back position resting at an angle and being substantially supported by the back of said second support member and back portion of said angular member, whereas the technician can now observe the said denture models in a straight on manner.

24. The device of claim 1 in which said dental articulator is made of plastic.

25. The device of claim 1 in which said dental articulator is made of metal.

26. The device of claim 1 in which said incisal guide is between said condylar joint and said denture models.

27. The device of claim 1 in which said first support member is movable to simulate actual centrix, lateral and protrusive jaw movements.

28. The device of claim 1 in which said upper support member is movable to multiple positions, said positions being held by spring tension on said ball.

29. The device of claim 1 in which said dental articulator comprises a non-glare surface.

30. The device of claim 29 in which said non-glare surface is provided by sand blasting.

31. The device of claim 1 in which said retaining means to hold denture models will hold plaster or plasterless molds.

32. The device of claim 1 in which said dental articulator is designed to be hand friendly.

* * * * *